United States Patent [19]

Nishi et al.

[11] Patent Number: 4,857,542
[45] Date of Patent: Aug. 15, 1989

[54] PROPHYLACTIC AND THERAPEUTIC COMPOSITION FOR CIRCULATORY DISORDERS AND METHOD OF TREATMENT

[75] Inventors: Hiroyoshi Nishi; Toshiaki Watanabe; Satoshi Yuki, all of Ami; Yasuhiro Morinaka, Tsuchiura; Katsuhiko Iseki, Abiko; Hiroko Sakurai, Minori, all of Japan

[73] Assignee: Mitsubishi Chemical Industries Limited, Tokyo, Japan

[21] Appl. No.: 122,516

[22] Filed: Nov. 19, 1987

Related U.S. Application Data

[63] Continuation-in-part of Ser. No. 862,091, May 12, 1986, abandoned.

[30] Foreign Application Priority Data

May 20, 1985 [JP] Japan ................. 60-105798
Nov. 7, 1985 [JP] Japan ................. 60-248057

[51] Int. Cl.[4] .............................. A61K 31/415
[52] U.S. Cl. ........................... 514/404; 514/405
[58] Field of Search .................... 514/404, 405

[56] References Cited

U.S. PATENT DOCUMENTS

| | | | |
|---|---|---|---|
| 3,514,465 | 5/1970 | Posselt et al. | 260/296 |
| 3,658,845 | 4/1972 | Posselt et al. | 260/330.5 |
| 3,781,439 | 12/1973 | Zoni et al. | 514/405 |
| 4,000,294 | 12/1976 | Möller et al. | 514/404 |
| 4,005,215 | 1/1977 | Möller et al. | 514/404 |
| 4,053,621 | 10/1977 | Möller et al. | 514/404 |
| 4,112,227 | 9/1978 | Möller et al. | 514/404 |
| 4,288,446 | 9/1981 | Möller et al. | 514/404 |
| 4,670,460 | 6/1987 | Mardin et al. | 514/404 |
| 4,698,344 | 10/1987 | Sasse et al. | 514/404 |

FOREIGN PATENT DOCUMENTS

| | | | |
|---|---|---|---|
| 47-29900 | 8/1972 | Japan | 514/404 |
| 47-47734 | 9/1972 | Japan | 514/404 |
| 52-77088 | 6/1977 | Japan | 514/404 |

OTHER PUBLICATIONS

Chem. Abst. 73:45404h, (1970)–Williams et al.
Chem. Abst. 101:222712(b), (1984)–Mardin et al.
Chem. Abst. 102:17649r, (1985)–Moeller et al.
Chem. Abst. 102:56154v, (1985)–Bayer A.G.
"Stroke", vol. 8, No. 1, Jan.–Feb. 1977, pp. 51–57.
"Cardiovascular Research", 14, 1980, pp. 371–395.

Primary Examiner—Frederick E. Waddell
Attorney, Agent, or Firm—Frishauf, Holtz, Goodman & Woodward

[57] ABSTRACT

A prophylactic and therapeutic agent for circulatory disorders, comprising a pyrazolone derivative of the formula:

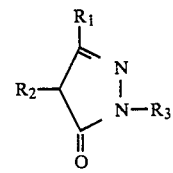

wherein $R_1$ represents a hydrogen atom, an aryl group, an alkyl group having 1 to 5 carbon atoms or an alkoxycarbonylalkyl group having a total carbon number of 3 to 6; $R_2$ represents a hydrogen atom, an aryloxy group, an arylmercapto group, an alkyl group having 1 to 5 carbon atoms or hydroxyalkyl group having 1 to 3 carbon atoms; or $R_1$ and $R_2$ taken together represent an alkylene group having 3 to 5 carbon atoms; $R_3$ represents a hydrogen atom, an alkyl group having 1 to 5 carbon atoms, a cycloalkyl group having 5 to 7 carbon atoms, a hydroxyalkyl group having 1 to 3 carbon atoms, a benzyl group, a naphthyl group, or a phenyl group which is unsubstituted or substituted with 1 to 3 substituents which are the same or different selected from the group consisting of alkyl groups having 1 to 5 carbon atoms, alkoxy groups having 1 to 5 carbon atoms, hydroxyalkyl groups having 1 to 3 carbon atoms, alkoxycarbonyl groups having total carbon number of 2 to 5, alkylmercapto groups having 1 to 3 carbon atoms, alkylamino groups having 1 to 4 carbon atoms, dialkylamino groups having total carbon number of 2 to 8, halogen atoms, trifluoromethyl group, carboxyl group, cyano group, hydroxyl group, nitro group, amino group and acetamide group, or a pharmaceutically acceptable salt thereof as an active ingredient.

The agent of the present invention is useful as a prophylactic and therapeutic agent for circulatory disorders, particularly as an inhibitor agaisnt lipid peroxidation and/or an agent for normalizing cerebral dysfunctions.

19 Claims, No Drawings

PROPHYLACTIC AND THERAPEUTIC COMPOSITION FOR CIRCULATORY DISORDERS AND METHOD OF TREATMENT

This application is a continuation-in-part, of application Ser. No. 862,091, filed May 12, 1986, now abandoned.

BACKGROUND OF THE INVENTION

This invention relates to a prophylactic and therapeutic agent for circulatory disorders, more particularly to a prophylactic and therapeutic agent for cerebral, cardiac or peripheral circulatory disorders accompanied with various ischemic diseases, especially to a prophylactic and therapeutic agent for circulatory disorders which is useful as an inhibitor against lipid peroxidation and/or an agent for normalizing cerebral dysfunctions.

In the specification, the term "circulatory disorders" means diseases due to circulatory disorder.

In cerebral, cardiac or peripheral circulatory disorders, as a result of ischemia (the state where little blood is supplied to tissues), active oxygens (OH.radical, superoxide, etc.) formed in the tissues thereround act on unsaturated fatty acids including arachidonic acid liberated from cell membranes, to form peroxidized lipids. Such changes will occur not only during ischemia, but also further will be accelarated and advanced by reoxidation through the blood refeeding after the ischemia to cause damage of cell membrane enriched in unsaturated fatty acids, destruction of surrounding tissues, destruction of blood vessel endothelium, blood vessel spasms or cerebral edema, etc., and the condition of disease will be advanced according to a vicious circle of a series of these reactions, as is well known in the art ("Cerebral Ischemia and Cell Disorder", edited by Takao Asano, Neuron Co., 1980; "Cerebral Ischemia and Free Radical", edited by Takao Asano, Neuron Co., 1983).

Accordingly, if lipid peroxidation by active oxygen could be inhibited, it would be possible to prevent destruction of cell membrane, destruction of blood vessel endothelium, blood vessel spasm, cerebral edema, etc., and give a prophylactic or therapeutic agent for circulatory disorders of a new type which can act on the cause of a disease, as different from the medicines of the prior art which ameliorates circulation by increasing the blood flow. Particularly, in recent years, effectiveness of such vasodilators is considerted to be doubtful and it is even said to be rather an adverse effect in cerebral insufficiency in the acute stage, and therefore such a pharmaceutical is further becoming more important.

As described above, peroxidized lipids is considered to be formed by the action of active oxygen as a result of ischemia. As the medicines which can inhibit lipid peroxidation by active oxygen, there have been known vitamin E, idebenone represented by the following formula:

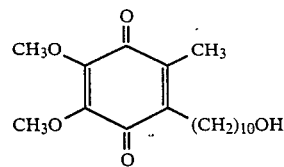

(Biochemical and Biophysical Research Communications 125, 1046 (1984); Report from Takeda Kenkyusho 44, 30 (1985)) and nizofenone represented by the following formula:

(Journal of Neurochemistry, 37, 934 (1981)).

However, these medicines have drawbacks such that vitamin E has only unsatisfactory action, that idebenone and nizofenone are prepared by lengthy synthetic routes, that idebenone is considered to involve a problem in formation of a preparation for injection due to difficulty in solubilizing in water and also that nizofenone has potent central nervous system depressant activity [Study of Pharmaceuticals (Iyakuhin Kenkyu) 16, 1 (1985)].

Particularly, as the cerebral circulatory disorders, there may be mentioned various cerebral diseases such as cerebrovascular disorders, cerebral dysfunctions, vascular dementia, cerebrovascular tissue lesions accompanied with aging, etc. In these diseases, symptoms such as consciousness disorders, lowering in memory, etc., based on cerebral dysfunctions, namely the abnormal pattern of electroencephalogram will be caused. Therefore, as the medicine to be used for prophylaxis and therapy of these cerebral disorders, those having antagonistic action against drowsy pattern of electroencephalogram during cerebral function abnormality (abnormal electroencephalogram) (hereinafter referred to as "electroencephalogram normalizing action") have been desired.

As a medicine having such pharmacological activity, thyrotropine releasing hormone (TRH) having a chemical structure of L-pyrroglutamyl-L-histidyl-L-prolineamide has been known [Neuropharmacology, 14, 489 (1975); Journal of Pharmacology and Experimental Therapeutics 193, 11 (1975)]. However, TRH exhibites an action which is deemed to be a side action in clinic, also against electroencephalogram under normal state. Also, since TRH is a tripeptide, there is a fear that it has a problem in stability in living body or absorption by oral administration, and the dosage form at the present time is only by way of intravenous administration.

Various pyrazolone derivatives have been known in the art.

Japanese Unexamined Patent Publication No. 13766/1976 discloses a pyrazolin-5-one derivative represented by the following formula and its use as antithrombus agent:

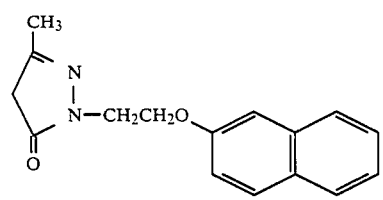

Japanese Unexamined Patent Publication No. 141517/1984 discloses use of the same compound as a therapeutic agent for cardiac infarction, inflammation, astham, etc., after myocardial ischemia.

Japanese Unexamined Patent Publication No. 175469/1984 discloses a pyrazolin-5-one derivative of the following formula and its use as a lipoxygenase inhibitor:

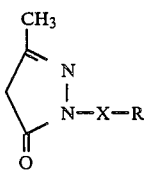

(wherein X represents a group $-CH_2CH_2O-$, $-CH_2CH_2S-$, etc., and R represents an aryl group).

Japanese Patent Publication No. 512/1984 discloses a pyrazolin-5-one derivative and its use as a diuretic, antihypertensive, and antithrombosis:

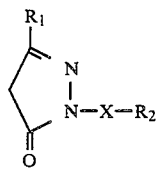

(wherein $R_1$ represents a hydrogen atom or an amino group, $R_2$ an aryl group and X represents a group $-CH_2CH_2-$, etc.).

However, these derivatives are not of the type in which all the aryl groups are bonded directly to the 1-position of the pyrazolin-5-one nucleus, and there is no description about the effect on cerebral dysfunctions including electroencephalogram normalizing action at all.

Also, West Germany Patent No. 28 36 891 discloses a pyrazolin-5-one derivative of the following formula and its use as antiinflammatory agent:

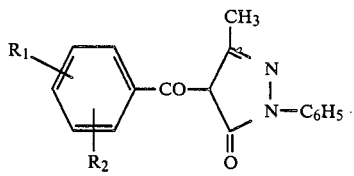

(wherein $R_1$ and $R_2$ represent a hydrogen atom or a substituent).

However, there is no description about the action of inhibiting lipid peroxidation by active oxygen. Also, while the compound represented by the formula (B) is stated to be effective in models of ischemic heart diseases using rats, rabbits and dogs, it is ineffective in a model using pigs, of which circulation state is approximate to that of human heart. This result well coincides with the report that it is ineffective for ischemic heart diseases in human being (European Journal of Pharmacology, 114, 189 (1985)). Also, there is no description about a specific action concerning protection after recirculation of cerebral ischemia.

SUMMARY OF THE INVENTION

Accordingly, the present inventors have studied intensively in order to provide a prophylactic and therapeutic agent for circulatory disorders in humans and mammals, more particularly a prophylactic and therapeutic agent for cerebral, cardiac or peripheral circulatory disorders accompanied with various ischemic diseases, especially a prophylactic and therapeutic agent for circulatory disorders which is useful as an inhibitor against lipid peroxidation and/or an agent for normalizing cerebral dysfunctions. Consequently, they have found that a pyrazolone derivative represented by the following Formula (I) has a potent inhibitory action against lipid peroxidation, and has an antagonistic action against browsy pattern of electroencephalogram in an animal model under the state approximate to the practical condition of disease and protective action such as restration of electroencephalogram after recirculation of cerebral ischemia, and thus it is useful as a prophylactic and therapeutic agent for circulatory disorders:

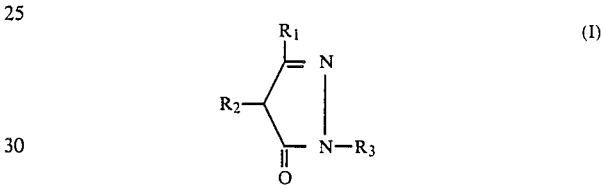

wherein $R_1$ represents a hydrogen atom, an aryl group, an alkyl group having 1 to 5 carbon atoms or an alkoxycarbonylalkyl group having a total carbon number of 3 to 6; $R_2$ represents a hydrogen atom, an aryloxy group, an arylmercapto group, an alkyl group having 1 to 5 carbon atoms or hydroxyalkyl group having 1 to 3 carbon atoms; or $R_1$ and $R_2$ taken together represent an alkylene group having 3 to 5 carbon atoms; $R_3$ represents a hydrogen atom, an alkyl group having 1 to 5 carbon atoms, a cycloalkyl group having 5 to 7 carbon atoms, a hydroxyalkyl group having 1 to 3 carbon atoms, a benzyl group, a naphthyl group, or a phenyl group which is unsubstituted or substituted with 1 to 3 substituents which are the same or different selected from the group consisting of alkyl groups having 1 to 5 carbon atoms, alkoxy groups having 1 to 5 carbon atoms, hydroxyalkyl groups having 1 to 3 carbon atoms, alkoxycarbonyl groups having total carbon number of 2 to 5, alkylmercapto groups having 1 to 3 carbon atoms, alkylamino groups having 1 to 4 carbon atoms, dialkylamino groiups having total carbon number of 2 to 8, halogen atoms, trifluoromethyl group, carboxyl group, cyano group, hydroxyl group, nitro group, amino group and acetamide group, The present invention has been accomplished on the basis of such a finding.

The prophylactic and therapeutic agent for circulatory disorders of the present invention comprises a pyrazolone derivative represented by the above Formula (I) or its pharmaceutically acceptable salts as the active ingredient.

The compound (I) to be used in the present invention can also take the structures shown by the following Formula (I') or (I''):

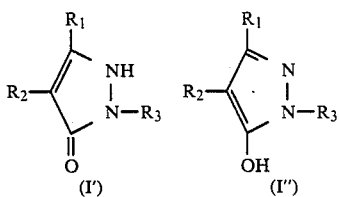

accordingly, the compounds having the structure of the above formula (I') or (I'') are also included within the active ingredient of the present invention.

DESCRIPTION OF THE PREFERRED EMBODIMENTS

In the above formula (I), the aryl group represented by $R_1$ may include a phenyl group and phenyl groups which are substituted with substituents such as methyl, butyl, methoxy, butoxy, hydroxy groups and a chlorine atom, etc. The alkyl group having 1 to 5 carbon atoms represented by $R_1$, $R_2$ and $R_3$ may include methyl, ethyl, propyl, isopropyl, butyl, isobutyl, sec-butyl, tertbutyl, pentyl groups and the like. The alkoxycarbonylalkyl group having total carbon number of 3 to 6 represented by $R_1$ may include methoxycarbonylmethyl, ethoxycarbonylmethyl, propoxycarbonylmethyl, methoxycarbonylethyl, methoxycarbonylpropyl groups and the like. The aryloxy groups represented by $R_2$ may include phenoxy, p-methylphenoxy, p-methoxphenoxy, p-chlorophenoxy, p-hydroxyphenoxy groups and the like. The arylmercapto group represented by $R^2$ may include phenylmercapto, p-methylphenylmercapto, p-methoxypenylmercapto, p-chlorophenylmercapto, p-hydroxyphenylmercapto groups and the like. The hydroxyalkyl group having 1 to 3 carbon atoms represented by $R_2$ or $R_3$ may include hydroxymethyl, 2-hydroxyethyl, 3-hydroxypropyl groups and the like. The cycloalkyl group having 5 to 7 carbon atoms represented by $R_3$ may include cyclopentyl, cyclohexyl, cycloheptyl groups and the like. As the substituent for the phenyl group in the definition of $R_3$, the alkoxy group having 1 to 5 carbon atoms may include methoxy, ethoxy, propoxy, isopropoxy, butoxy, pentyloxy groups and the like; the alkoxycarbonyl group having total carbon number of 2 to 5 may include methoxycarbonyl, ethoxycarbonyl, propoxycarbonyl, butoxycarbonyl groups and the like; the alkylmercapto group having 1 to 3 carbon atoms may include methylmercapto, ethylmercapto, propylmercapto groups and the like; the alkylamino group having 1 to 4 carbon atoms may include methylamino, ethylamino, propylamino, butylamino groups and the like; and dialkylamino group having total carbon number of 2 to 8 may include dimethylamino, diethylamino, dipropylamino, dibutylamino groups and the like.

Specific examples of the compound (I) to be used in the present invention are shown below.
3-Methyl-1-phenyl-2-pyrazolin-5-one;
3-Methyl-1-(2-methylphenyl)-2-pyrazolin-5-one;
3-Methyl-1-(3-methylphenyl)-2-pyrazolin-5-one;
3-Methyl-1-(4-methylphenyl)-2-pyrazolin-5-one;
3-Methyl-1-(3,4-dimethylphenyl)-2-pyrazolin-5-one;
1-(4-Ethylphenyl)-3-methyl-2-pyrazolin 5-one;
3-Methyl-1-(4-propylphenyl)-2-pyrazolin-5-one;
1-(4-Butylphenyl)-3-methyl-2-pyrazolin-5-one;
1-(3-Trifluoromethylphenyl)-3-methyl-2-pyrazolin-5-one;
1-(4-Trifluoromethylphenyl)-3-methyl-2-pyrazolin-5-one;
1-(2-Methoxyphenyl)-3-methyl-2-pyrazolin-5-one;
1-(3-Methoxyphenyl)-3-methyl-2-pyrazolin-5-one;
1-(4-Methoxyphenyl)-3-methyl-2-pyrazolin-5-one;
1-(3,4-Dimethyoxyphenyl)-3-methyl-2-pyrazolin-5-one;
1-(4-Ethoxyphenyl)-3-methyl-2-pyrazolin-5-one;
3-Methyl-1-(4-propoxyphenyl)-2-pyrazolin-5-one;
1-(4-Butoxyphenyl)-3-methyl-2-pyrazolin-5-one;
1-(2-Chlorophenyl)-3-methyl-2-pyrazolin-5-one;
1-(3-Chlorophenyl)-3-methyl-2-pyrazolin-5-one;
1-(4-Chlorophenyl)-3-methyl-2-pyrazolin-5-one;
1-(3,4-Dichlorophenyl)-3-methyl-2-pyrazolin-5-one;
1-(4-Bromophenyl)-3-methyl-2-pyrazolin-5-one;
1-(4-Fluorophenyl)-3-methyl-2-pyrazolin-5-one;
1-(3-Chloro-4-methylphenyl)-3-methyl-2-pyrazolin-5-one;
1-(3-Methylmercaptophenyl)-3-methyl-2-pyrazolin-5-one;
1-(4-Methylmercaptophenyl)-3-methyl-2-pyrazolin-5-one;
4-(3-Methyl-5-oxo-2-pyrazolin-1-yl)benzoic acid;
1-(4-Ethoxycarbonylphenyl)-3-methyl-2-pyrazolin-5-one;
3-Methyl-1-(4-nitrophenyl)-2-pyrazolin-5-one;
3-Ethyl-1-phenyl-2-pyrazolin-5-one;
1-Phenyl-3-propyl-2-pyrazolin-5-one;
1,3-Diphenyl-2-pyrazolin-5-one;
3-Phenyl-1-(p-tolyl)-2-pyrazolin-5-one;
1-(4-Methoxyphenyl)-3-phenyl-2-pyrazolin-5-one;
1-(4-Chlorophenyl)-3-phenyl-2-pyrazolin-5-one;
3,4-Dimethyl-1-phenyl-2-pyrazolin-5-one;
4-Isobutyl-3-methyl-1-phenyl-2-pyrazolin-5-one;
4-(2-Hydroxyethyl)-3-methyl-1-phenyl-2-pyrazolin-5-one;
3-Methyl-4-phenoxy-1-phenyl-2-pyrazolin-5-one;
3-Methyl-4-phenylmercapto-1-phenyl-2-pyrazolin-5-one;
3,3a,4,5,6,7-Hexahydro-2-phenyl-2H-indazol-3-one;
3-(Ethoxycarbonylmethyl)-1-phenyl-2-pyrazolin-5-one;
1-Phenyl-2-pyrazolin-5-one;
3-Methyl-2-pyrazolin-5-one;
1,3-Dimethyl-2-pyrazolin-5-one;
1-Ethyl-3-methyl-2-pyrazolin-5-one;
1-Butyl-3-methyl-2-pyrazolin-5-one;
1-(2-Hydroxyethyl)-3-methyl-2-pyrazolin-5-one;
1-Cyclohexyl-3-methyl-2-pyrazolin-5-one;
1-Benzyl-1-methyl-2-pyrazolin-5-one;
1-(α-naphthyl)-3-methyl-2-pyrazolin-5-one;
1-Methyl-3-phenyl-2-pyrazolin-5-one;
1-Methyl-3-(4-methylphenyl)-2-pyrazolin-5-one;
1-(4-Butylphenyl)-3-phenyl-2-pyrazolin-5-one;
3-(4-Methoxyphenyl)-1-methyl-2-pyrazolin-5-one;
3-(4-Butoxyphenyl)-1-methyl-2-pyrazolin-5-one;
3-(4-Chlorophenyl)-1-methyl-2-pyrazolin-5-one;
3-(4-Hydroxyphenyl)-1-methyl-2-pyrazolin-5-one;
1-(3,4-Dihydroxyphenyl)-3-methyl-2-pyrazolin-5-one;
1-(2-Hydroxyphenyl)-3-methyl-2-pyrazolin-5-one;
1-(3-Hydroxyphenyl)-3-methyl-2-pyrazolin-5-one;
1-(4-Hydroxyphenyl)-3-methyl-2-pyrazolin-5-one;
1-(3,4-Hydroxyphenyl)-3-phenyl-2-pyrazolin-5-one;
1-(4-Hydroxyphenyl)-3-phenyl-2-pyrazolin-5-one;
1-(4-Hydroxymethylphenyl)-3-methyl-2-pyrazolin-5-one;
1-(4-Aminophenyl)-3-methyl-2-pyrazolin-5-one;
1-(4-Methylaminophenyl)-3-methyl-2-pyrazolin-5-one;
1-(4-Ethylaminophenyl)-3-methyl-2-pyrazolin-5-one;
1-(4-Butylaminophenyl)-3-methyl-2-pyrazolin-5-one;

1-(4-Dimethylaminophenyl)-3-methyl-2-pyrazolin-5-one;
1-(Acetamidophenyl)-3-methyl-2-pyrazolin-5-one;
1-(4-Cyanophenyl)-3-methyl-2-pyrazolin-5-one;

Some of the compounds to be used in the present invention are known compounds which can be used as the intermediate starting materials for dyes, etc., but their uses for pharmaceuticals have not been known.

Particularly, 3-methyl-1-phenyl-2-pyrazolin-5-one of the Formula (I-A):

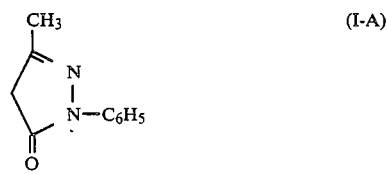

is a known compound which is used as starting materials for dyes and is a metabolite of antipyrine [Drug Metabolism and Disposition, 6, 228 (1978)], but its use as a pharmaceutical has not been known. However, this compound has been already evidenced to be high in safety (mouse intraperitoneal administration $LD_{50}$ 2012 mg/kg; rat oral administration $LD_{50}$ 3500 mg/kg) [Registry of Toxic Effects of Chemical Substances, 1981–1982] and also free from carcinogenicity [National Cancer Institute Report, 1978, 89].

Pharmaceutically acceptable salts of the compound (I) to be used in the present invention include salts with mineral acids such as hydrochloride acid, sulfuric acid, hydrobromic acid, phosphoric acid, etc.; salts with organic acids such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid, tartaric acid, etc.; salts with alkali metals such as sodium, potassium, etc.; salts with alkaline earth metals such as magnesium, calcium, etc.; salts with amines such as ammonia, tris(hydroxymethyl)aminomethane, N,N-bis(hydroxyethyl)-piperazine, 2-amino-2-methyl-1-propanol, ethanolamine, N-methylglucamine, L-glucamine, etc.

The compounds to be used in the present invention can be synthesized according to any desired method suited for the purpose, and an example of the preferable methods is shown below.

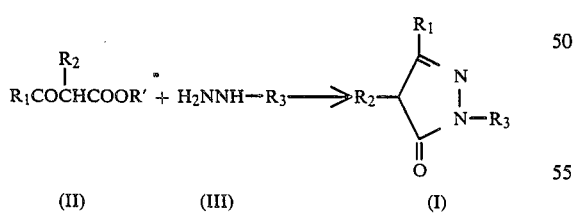

wherein $R_1$, $R_2$ and $R_3$ have the same meanings as defined above, and R' represents an alkyl group having 1 to 5 carbon atoms.

More specifically, the compound (I) can be obtained by allowing a β-keto acid derivative represented by the Formula (II) and a hydradine derivative represented by the Formula (III) to react in either the presence or absence of a solvent such as alcohols (e.g. methanol, ethanol, etc.) or aromatics (e.g. benzene, toluene, etc.), optionally in the presence of a catalyst such as a base (e.g. potassium carbonate, sodium methoxide, sodium ethoxide, sodium hydroxide, potassium hydroxide, sodium acetate, etc.), a mineral acid (e.g. hydrochloric acid, sulfuric acid, hydrobromic acid, etc.) or an organic acid (e.g. acetic acid, para-toluenesulfonic acid, etc.), at a temperature of 10° to 200° C.

Particularly, the compound (Formula I-A) as described above can be prepared by allowing ethyl acetoacetate and phenylhydradine to react in the presence or absence of a solvent, optionally in the presence of a catalyst such as a base or an acid [Beilstein, 24, 20].

Also, depending on the substituent on the aryl group of $R_3$, desired compounds can be synthesized as shown below.

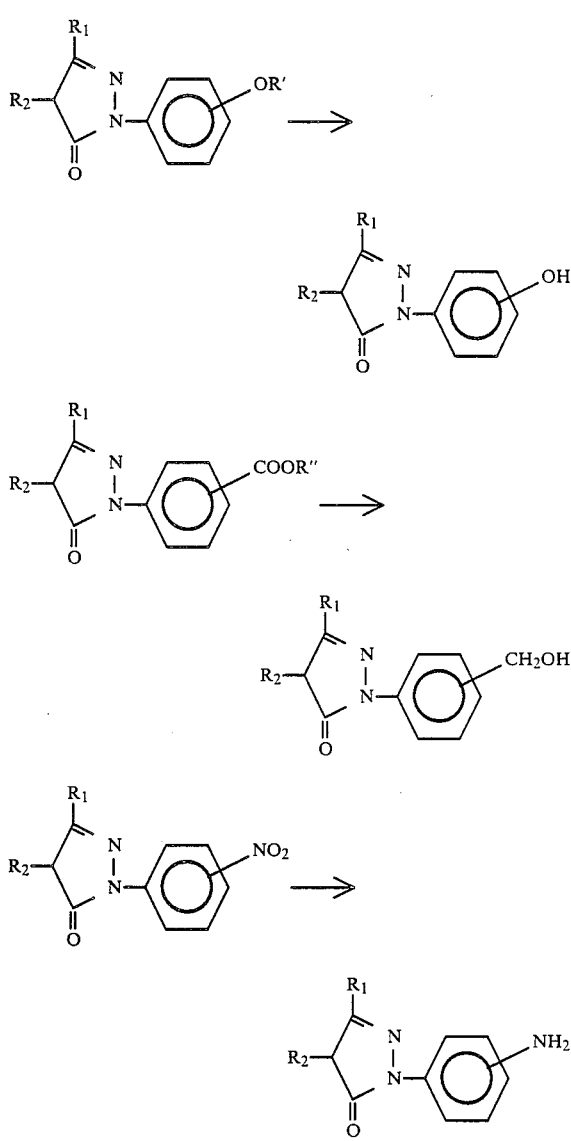

wherein $R_1$, $R_2$ and R' have the same meanings as defined above, and R" represents a hydrogen atom, an alkyl group having 1 to 5 carbon atoms or an alkoxycarbonyl group having total carbon number of 2 to 6.

The desired compound wherein said substituent is a hydroxyl group can be obtained by, for example, decomposing an appropriate alkoxy group with hydrobromic acid or a Lewis acid. The desired compound wherein said substituent is a hydroxymethyl group can be obtained by, for example, reducing a carboxylic acid or its derivative with an appropriate reducing agent such as lithium aluminum hydride, sodium boron hydride or diborane. The desired compound wherein said substituent is an amino group can be obtained by, for example, reducing a nitro group under appropriate conditions with, for example, hydrogen-Pd/C, hydrochloric acid-stannic chloride.

In applying clinically the compound (I) in the case of using it orally, it is preferable to administer the compound (I) at a dose of 1 to 100 mg 1 to 3 times/day for an adult (human). In the case of intravenous injection, it is preferable to administer the compound (I) at a dose of 0.01 to 10 mg 2 to 5 times/day for an adult or to inject these doses continuously by way of instillation. On the other hand, in the case of intrarectal administration, it is preferable to administer the compound (I) at a dose of 1 to 100 mg 1 to 3 times/day. It is more preferable to increase or decrease adequately the above doses depending on the age, the condition and specifics of the patient and/or the specifics of the disease and symptoms. Other mammals would be treated within the same dosage range modified for relative body weight.

Also, in the case of oral or intrarectal administration, the compound may be used as a delayed-release preparation.

In forming preparations, it is generally practiced to use a composition containing the compound (I) or at least one pharmaceutically acceptable salts thereof together with a carrier, excepient or other additives for pharmaceuticals conventionally used. Pharmaceutical carriers may be either solid or liquid, and examples of solid carriers include lactose, kaolin, sucrose, crystalline cellulose, corn starch, talc, agar, pectin, acacia, stearic acid, magnesium stearate, lecithin, sodium chloride, etc.

Examples of liquid carriers include syrup, glycerine, peanuts oil, polyvinylpyrrolidone, olive oil, ethanol, benzyl alcohol, propyleneglycol, water, etc.

Various preparation forms can be employed and, when using a solid carrier, they can be formed into tablets, powders, granules, hard gelatin capsules, suppositories or troches. The amount of the solid carrier can be widely varied, but it is preferably about 1 mg to about 1 g.

When employing a liquid carrier, it can be made into a syrup, emulsion, soft gelatin capsules, further sterilized injectable solutions or aqueous or non-aqueous suspensions filled in ampoules.

Also, the compound (I) can be also used as a cyclodextrin clathrate compound thereof or through procedure of incorporating it in a liposome.

The prophylactic and therapeutic agent for circulatory disorders of the present invention has excellent actions, can be also administered orally and is useful as prophylactic or therapeutic agent for circulatory disorders accompanied with various ischemic diseases or various diseases based thereon, that is, cerebrovascular disorders such as cerebral infarction, cerebral apoplexy, etc., or lowering in cerebral functions caused by such disorders, various cerebral diseases such as vascular dementia, cerebrovascular tissue lesion, accompanied with aging, etc., various heart diseases based on myocardial ischemia such as myocardial infarction, cardiac insufficiency angina pectoris, etc., and various peripheral circulation disorders, etc.

Further, the prophylactic and therapeutic agent for circulatory disorders of the present invention is widely applicable for therapy of trauma at the head portion, intracerebral hemorrhage, subarachidonic hemorrhage, cerebral arterio-sclerosis, cerebral infarction, cerebral embolism, etc.; therapy at the acute stage of ischemic cerebrovascular disorders caused by said diseases such as cerebral edema, etc.; thereby and prevention of recurrence of various diseases recognized at the subacute stage and chronic stage of cerebrovascular disorders after elongation of life after elapse of said acute stage, such as lowering in cerebral dysfunctions, typically vascular dementia, etc.; therapy of various cerebral diseases complicated by the advance of cerebrovascular tissue lesion accompanied with aging; clearing of obnubilation which appears at the acute stage and chronic stage of cardiovascular disorders; as well as emergence from anesthesia, etc. Also, it has a specific feature, as different from TRH, of normalizing selectively only the electroencephalogram under abnormal state substantially without exhibiting any action on the electroencephalogram under normal state.

The present invention is described in more detail by referring to synthetic examples and examples, but these are not intended to limit the scope of the present invention.

Synthetic example 1

Into 50 ml of ethanol, 13.0 g of ethyl acetoacetate and 10.8 g of phenylhydrazine were added, and the mixture was refluxed under stirring for 3 hours. After left to cool, the precipitated crystals were filtered and recrystallized from ethanol to obtain 11.3 g of 3-methyl-1-phenyl-2-pyrazolin-5-one (Compound No. 1) as colorless crystals.

Yield 65%, m.p. 127.5°–128.5° C.

Synthetic examples 2–43

In the same manner as Synthetic example 1, the Compounds No. 2–43 shown in Table 1 were synthesized.

Synthetic example 44

An amount of 1.80 g of 1-(2-methoxyphenyl)-3-methyl-2-pyrazolin-5-one was added into a mixture of 18 ml of 47% hydrobromic acid and 18 ml of acetic acid, and the mixture were refluxed under stirring for 6.5 hours. After evaporation of the solvent, an aqueous $NaHCO_3$ solution was added to the residue to adjust to pH 4 and the mixture was extracted with ethyl acetate. The organic layer was dried and concentrated, followed by recrystallization of the residue from ethanol to give 1.19 g of 1-(2-hydroxyphenyl)-3-methyl-2-pyrazolin-5-one (Compound No. 44) as colorless crystals.

Yield 67%, m.p. 212.5°–214° C.

Synthetic examples 45–48

In the same manner as Synthetic example 44, Compounds No. 45–48 shown in Table 1 were synthesized.

Synthetic example 49

Into 250 ml of anhydrous chloroform were added 5.0 g of 4-(3-methyl-5-oxo-2-pyrazolin-1-yl)benzoic acid and 25 ml of triethylamine and, further under ice-cooling, 12.5 ml of ethyl chlorocarbonate was added dropwise into the mixture. After evaporation of the solvent, the residue was dissolved in 200 ml of THF, the insolubles were filtered off, and then a solution of 2.08 g of $NaBH_4$ dissolved in 60 ml of water was added dropwise into the filtrate, followed by stirring at room temperature for 2 hours. After evaporation of the solvent, water was added to the residue, and the mixture was adjusted with dil. hydrochloric acid to pH 4–5 and then extracted with chloroform. The organic layer was dried, concentrated and purified on silica gel column chromatograph with the use of chloroform-ethanl (100:1) as eluant, followed by recrystallization from chloroform-ethyl ether to give 1.16 g of 1-(4-hydroxymethyl-phenyl)-3-methyl-2-pyrazolin-5-one as colorless crystals.

Yield 35%, m.p. 139°–140° C.

Synthetic example 50

Into 310 ml of methanol, 500 mg of 3-methyl-1-(4-nitrophenyl)-2-pyrazolin-5-one was dissolved, 50 mg of 5% Pd/C and 0.6 ml of conc. hydrochloric acid were added to the solution, and the mixture was stirred under hydrogen atmosphere to consume the calculated amount of hydrogen. Then, the catalyst was filtered off and the filtrate was concentrated. The residue was recrystallized from methanol-ethyl ether to give 409 mg of 1-(4-aminophenyl)-3-methyl-2-pyrazolin-5-one dihydrochloride (Compound No. 50) as pale brown crystals.

Yield 68%, m.p. 196°–200° C.

Synthetic example 51

In the same manner as Synthetic example 1, the Compound No. 51 shown in Table 1 was synthesized.

EXAMPLE 1

(1) Inhibitory action of lipid peroxidation (a) Preparation of brain homogenate

By use of Wister-strain male rat, brain homogenate was prepared following the procedure as described below. Chest was opened under anesthesia by intraperitoneal administration of 45 mg/kg of pentobarbital sodium, and a polyethylene tube was intubated into aorta from left ventricle to be fixed therein. Next, a brain perfusion was conducted through the tube with ice-cooled 50 mM phosphate-buffered physiological saline (pH 7.4) (hereinafter referred to as "PBS"), and the whole brain was extirpated. After removal of cerebellum, the wet weight of cerebrum was measured and, with addition of 9-fold amount of PBS, it was broken by a Teflon homogenizer in ice-water to be homogenized. After the brain homogenate was subjected to centrifugation at 4° C. at 2200 rpm for 10 minutes, 0.3 ml of the supernatant was apportioned into a light-shielding test tube equipped with a ground stopper, to provide a brain homogenate for evaluation of medicine.

(b) Evaluation of test medicine

To the brain homogenate produced in (a), 0.6 ml of PBS and 10 μl of ethanolic solution of a test medicine were added (to a final concentration of 500 μM or a concentration at a common ratio of 3 between 0.3 and 100 μm), and the mixture was heated in a warm bath at 37° C. for 30 minutes. Subsequently, after addition of 200 μl of an aqueous 35% perchloric acid solution, centrifugation was effected at 4° C. at 2600 rpm for 10 minutes to obtain a supernatant. Also, the same operation was performed by addition of 10 μl of ethanol (blank) in place of 10 μl ethanolic solution of the test medicine for measurement of blank.

(c) Quantitative determination of peroxidized lipid

To 0.1 ml of the supernatant obtained in (b), 0.2 ml of aqueous 8.1% sodium dodecyl sulfate solution, 1.5 ml of 20% acetate buffer (pH 3.5), 1.5 ml of aqueous 0.67% 2-thiobarbituric acid solution and 0.7 ml of distilled water, followed by mixing. Next, this mixture was heated in a boiling water bath for 60 minutes and then quenched with ice-water, and 1.0 ml of distilled water and 5.0 ml of a pyridine-butanol mixture (1:15) were added. After shaking for about 30 seconds, the mixture was subjected to centrifugation at 3000 rpm for 10 minutes, and the supernatant was provided as a sample for measurement of peroxidized lipid. A standard solution was prepared by addiing 0.1 ml of Lipoperoxide-test (containing 5 nmol/ml 1,1,3,3-tetraethoxypropane, produced by Wako Junyaku K.K.) in place of the brain homogenate obtained in (b).

The peroxidized lipid was measured by use of a fluoroescent spectrophotometer (model 204, produced by Hitachi Seisakusho K.K.) at an excitation wavelength of 515 nm and a fluorescence wavelength of 550 nm, and the peroxidized lipid quantity (TBA value) was determined according to the following formula:

$$TBA \text{ value} = 0.5 \times \frac{f}{F} \times \frac{1.1}{0.3} \times 10 \text{ (nmol/ml)}$$

F: fluorescence intensity of standard solution
f: fluorescence intensity of test medicine Then, inhibitory ratios at respective concentrations of test medicines relative to the TBA value of the blank in (b) were determined and IC$_{50}$ values were calculated according to the least-squares method. The results are shown in Table 1.

TABLE 1

| Compound No. | R$_1$ | R$_2$ | R$_3$ | m.p. (°C.) | IC$_{50}$ value (μM) |
|---|---|---|---|---|---|
| 1 | CH$_3$ | H |  | 127.5~128.5 | 18.2 |
| 2 | " | " | CH$_3$ 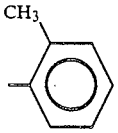 | 186~188 | 392.2 |

TABLE 1-continued
| Compound No. | R₁ | R₂ | R₃ | m.p. (°C.) | IC₅₀ value (μM) |
|---|---|---|---|---|---|
| 3 | " | " | 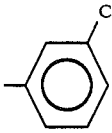 3-CH₃-phenyl | 110.5~112 | 8.0 |
| 4 | " | " | 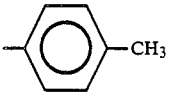 4-CH₃-phenyl | 134~134.5 | 6.3 |
| 5 | " | " | 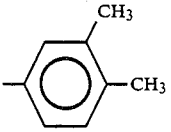 3,4-diCH₃-phenyl | 116~119 | 6.0 |
| 6 | " | " | 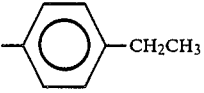 4-CH₂CH₃-phenyl | 147~149.5 | 4.2 |
| 7 | " | " | 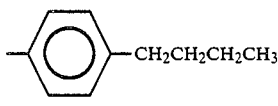 4-CH₂CH₂CH₂CH₃-phenyl | 96~97.5 | 2.2 |
| 8 | " | " | 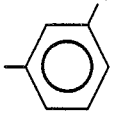 3-CF₃-phenyl | 124.5~126 | 3.9 |
| 9 | " | " | 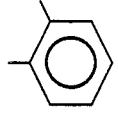 2-OCH₃-phenyl | 156~157 | 2129.0 |
| 10 | " | " | 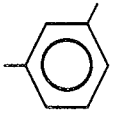 3-OCH₃-phenyl | 112.5~113 | 7.1 |
| 11 | " | " | 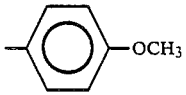 4-OCH₃-phenyl | 124~125 | 20.7 |
| 12 | " | " | 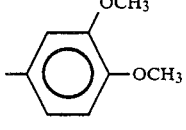 3,4-diOCH₃-phenyl | 157~158 | 23.0 |
| 13 | " | " | 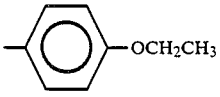 4-OCH₂CH₃-phenyl | 146.5~148 | 10.3 |

TABLE 1-continued
| Compound No. | R₁ | R₂ | R₃ | m.p. (°C.) | IC₅₀ value (μM) |
|---|---|---|---|---|---|
| 14 | " | " | 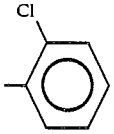 | 193~194.5 | 97.8 |
| 15 | " | " | 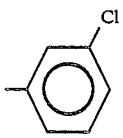 | 127~127.5 | 3.4 |
| 16 | " | " | 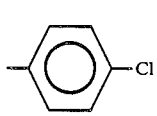 | 172~173 | 4.0 |
| 17 | " | " | 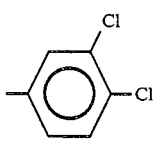 | 167.5~169 | 1.6 |
| 18 | CH₃ | H | 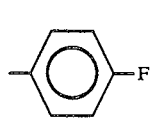 | 148~149 | 12.1 |
| 19 | " | " | 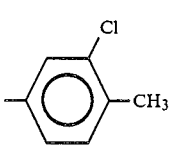 | 149~150 | 4.1 |
| 20 | " | " | 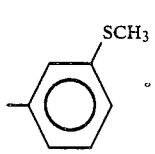 | 160~162 | 5.1 |
| 21 | " | " | 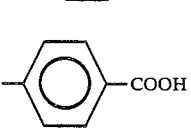 | 285 (decomposition) | (34.0%)* |
| 22 | " | " | 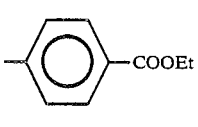 | 127~127.5 | 5.2 |
| 23 | " | " | 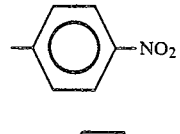 | 174~176 | 5.1 |
| 24 | CH₃CH₂— | " | 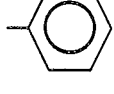 | 99.5~101.5 | 15.1 |
| 25 | CH₃CH₂CH₂— | " | " | 105~106 | 5.9 |
| 26 | 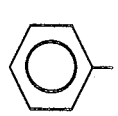 | " | " | 136.5~138 | 0.08 |

TABLE 1-continued

| Compound No. | R₁ | R₂ | R₃ | m.p. (°C.) | IC₅₀ value (μM) |
|---|---|---|---|---|---|
| 27 | " | " | 4-methylphenyl | 142~144 | 1.2 |
| 28 | " | " | 4-methoxyphenyl | 128~130 | 3.0 |
| 29 | " | " | 4-chlorophenyl | 162.5~164 | 1.2 |
| 30 | CH₃ | CH₃ | phenyl | 129~129.5 | 20.6 |
| 31 | " | (CH₃)₂CHCH₂— | " | 115~117 | 5.7 |
| 32 | " | HOCH₂CH₂— | " | 148~149 | (62.7%)* |
| 33 | " | phenyl-O— | " | 174~178 | 16.2 |
| 34 | " | phenyl-S— | " | 198~199.5 | 146.4 |
| 35 | —(CH₂)₄— |  | phenyl | 174~176.5 | 16.4 |
| 36 | EtOOCCH₂— | H | " | Oily product | 32.2 |
| 37 | CH₃ | " | H | 221~222.5 | (34.3%)* |
| 38 | " | " | CH₃ | 112~113 | (45.5%)* |
| 39 | " | " | —CH₂CH₂OH | 104~105 | (39.2%)* |
| 40 | " | " | cyclohexyl | 148~149 | 24.8 |
| 41 | " | " | —CH₂-phenyl | 172~175.5 | 32.9 |
| 42 | " | " | 1-naphthyl | 165~166 | 4.9 |
| 43 | phenyl- | " | CH₃ | 210~211 | 27.2 |

TABLE 1-continued

| Compound No. | R₁ | R₂ | R₃ | m.p. (°C.) | IC$_{50}$ value (μM) |
|---|---|---|---|---|---|
| 44 | CH₃ | " | 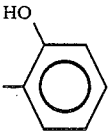 HO–⟨phenyl⟩ | 212.5~214 | 35.5 |
| 45 | " | " | 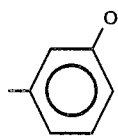 –⟨phenyl⟩–OH (meta) | 196~197 | 21.2 |
| 46 | " | " | 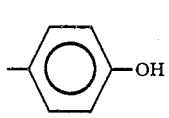 –⟨phenyl⟩–OH (para) | 230 (decomposition) | 23.9 |
| 47 | " | " | 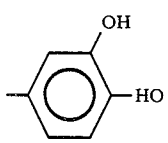 –⟨phenyl⟩(OH)(HO) | 196~200 (decomposition) | 1.3 |
| 48 | 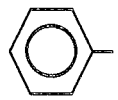 ⟨phenyl⟩ | " | 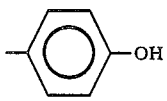 –⟨phenyl⟩–OH | 202 (decomposition) | 2.7 |
| 49 | CH₃ | H | 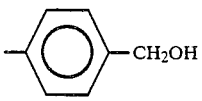 –⟨phenyl⟩–CH₂OH | 139~140 | 51.8 |
| 50 | " | " | 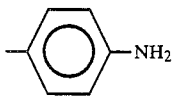 –⟨phenyl⟩–NH₂ (dihydrochloride) | 196~200 | 32.1 |
| 51 | H | " |  –⟨phenyl⟩ | 117~118 | 20.1 |

*Inhibitory percentage at 500 μM (2) Antagonistic action against drowsy pattern of electroencephalogram induced by phenobarbital or pentobarbital sodium salt A Wistar-strain male rat weighing about 400 g was intramasculary administered with 0.6 mg of d-tubocurarine to be immobilized and, while maintaining the rectal temperature at 37° to 38° C. under artificial respiration, the electroencephalogram of the left cerebral frontal cortex was measured and recorded. Also, within the left femoral artery and vein, cannulas for measurement of artery pressure and for administration of medicine were placed, respectively.

As the active ingredient of the present invention, sodium salt of the compound represented by Formula (I) was used and the respective doses of said active ingredient and 30 mg/kg of phenobarbital sodium salt (produced by Iwaki Seiyaku K.K.) (hereinafter called "PHB") or 5 mg/kg of pentobarbital sodium salt (hereinafter called PBT) were each dissolved in physiological saline and administered intravenously in a liquid amount of 1 ml/kg.

The action of the active ingredient of the present invention affecting the cortex electroencephalogram after PHB or PBT administration was investigated as follows; Namely, at the time of 5 minutes or later after PHB or PBT administration when increase of the slow-wave component can be clearly recognized on electroencephalogram, 1, 3, 10, 30 and 100 mg/kg of the active ingredient were administered. To the control group 1 ml/kg of physiological saline was intravenously administered.

Recording and analysis of electroencephalogram were continuously drawn together with artery pressure, heart rate and rectal temperature on the recorder through a multi-purpose monitoring recording device (model RM-85, produced by Nippon Koden K.K.). At the same time, electroencephalogram was recorded in data recorder (model A-65, produced by Sony K.K.), and compressed spectral array analysis was conducted by means of a computer for medical data processing (ATAC-450, produced by Nippon Koden K.K.).

By administration of 30 mg/kg of PHB, the cerebral cortical electroencephalogram becomes high voltage slow-wave, thus exhibiting clearly sleep-like electroencephalogram. Such an action persists for at least 3 hours or longer after the administration.

In contrast, when the active ingredient of the present invention was administered even in an amount of 100 mg/kg, not only the drowsy pattern of electroencephalogram as observed in the case of PHB, but also no appearance of low voltage fast-wave component (arousal pattern) was recognized at all.

From this fact, it has been found that the active ingredient of the present invention has no effect on normal electroencephalogram at all even when administered in a large amount.

However, when the active ingredient of the present invention was administered during appearance of the drowsy pattern of electroencephalogram after PHB or PBT administration, the drowsy pattern of electroencephalogram aws normalized depending on the dose thereof. The results are shown in Table 2.

TABLE 2

| Administered group | Results |
| --- | --- |
| Compound 1 | Antagonistic action at 1 mg/kg or higher |
| Compound 4 | Antagonistic action at 10 mg/kg or higher |
| Compound 11 | Antagonistic action at 10 mg/kg or higher |
| Compound 25 | Antagonistic action at 10 mg/kg or higher |
| Compound 31 | Antagonistic action at 10 mg/kg or higher |
| Control group | No antagonistic action |

(3) Protective action in cerebral ischemia recirculation model

A Wistar-strain male rat weighing about 400 g was administered intramascularly with 0.6 mg of di-tubocurarine to be immobilized and, after a trachea cannulation, the head portion was fixed under artificial respiration on a stereotaxic device. The head skin was cut open, cranial bone was bored, and then bipolar electrode for lead-out of electroencephalogram were placed on the surface of the subdural left frontal cerebral cortex. After the electrode was fixed with the cranial bone by use of dental cement, the animal was held on its back. Next, a cannula for measurement of systemic pressure was placed within the left femoral artery, and a cannula for additional administration of d-tubocurarine within the left femoral vein, respectively. The heart rate was measured and recorded by driving a heart rate meter with the artery wave.

After blood pressure, heart rate and various parameters of electroencephalogram were stabilized, 10 mg/kg of the active ingredient of the present invention prepared in a suspension so as to give 1 ml/kg in 1% tragacanth gum solution was administered directly into duodenum 30 minutes after cerebral ischemia loading. To the control group, only the 1% tragacanth gum solution of the same volume was administered similarly.

Ten to twenty minutes after administration of the medicine, while monitoring the electroencephalogram, blood pressure and heart rate on a multi-purpose monitoring recording device (RM-85 model, produced by Nippon Koden K.K.), the following operations were performed according to the methods shown below for cerebral ischemia loading.

First, ribs were set free at the left costicartilage end to open the chest. Next, cerebral blood flow was blocked for ten minutes by obstructing the left common carotid artery and the left subclavian artery exposed at the aorta originating portion at the same time, and then the brachiocephalic trunk by use of artery clips 30 minutes after administration of the medicine.

Recirculation of cerebral blood flow was effected by releasing at the same time the two artery clips mounted on the respective sites as mentioned above.

The protective action of the medicine for the disorder after recirculation of cerebral ischemia was examined by the presence of restoration of electroencephalogram, and survival time of animal after the recirculation.

During the experiment, the rectal temperature of the animal was maintained at 37° to 38° C. by use of a warming mat. Also, the rectal temperature was continuously drawn on the recorder together with electroencephalogram, femoral artery pressure and heart rate.

When cerebral ischemia was loaded for 10 minutes, the voltage of electroencephalogram was lowered immediately after ischemia until electroencephalogram became disappeared and leveled after elapse of about 15 seconds. Such flattening of electroencephalogram during loading of ischemia was recognized commonly in both of the control group and the group administered with the active ingredient of the present invention.

Even when cerebral ischemia for ten minutes was released and recirculated, no appearance of electroencephalogram was recognized at all in all the cases of the control group and flattering of electroencephalogram was continued to be maintained similarly as during loading of ischemia. By persistence of such a flattened electroencephalogram, the animals were dead 75 minutes after recirculation on an average.

However, in the group administered with the active ingredient of the present invention, electroencephalogram appeared by restoration during recirculation period, whereby the function of the cardiovascular system were activated and normalized simultaneously with restoration of the so called cerebral functions. As the overall results of these, the survival time of animals after recirculation was clearly elongated. The results are shown in Table 3.

TABLE 3

| Compound No. | Presence of electroencephalogram restoration |
| --- | --- |
| 1 | + |
| 4 | + |
| 11 | + |
| 13 | + |
| 16 | + |
| 25 | + |
| 30 | + |
| 31 | + |
| 35 | + |
| 40 | + |

Further, particularly for the case of employing the compound represented by the formula (I-A) (Compound No. 1) as the active ingredient, its dose was varied for evaluation of its protective action after recirculation of cerebral ischemia. As the result, in the group administered with the active ingredient of the present invention electroencephalogram appeared by restoration during recirculation period depending on the dose of 3 to 10 mg/kg, whereby the functions of the cardiovascular system were activated and normalized simultaneously with restoration of the so called cerebral functions. As the overall result of these, the survival time of animals after the recirculation was clearly elongated. The results are shown in Table 4.

TABLE 4

| Administered group | | Animal No. | Survival time after recirculation (min.) | Presence of electroencephalogram restoration | Judgement of action* |
|---|---|---|---|---|---|
| Active ingredient of the invention | 3 mg/kg | 1 | 85 | + | + |
| | | 2 | 126 | − | − |
| | | average | 106 | | |
| | 10 mg/kg | 1 | 46 | + | + |
| | | 2 | 140 | + | + |
| | | 3 | 164 | + | + |
| | | average | 117 | | |
| Control group | | 1 | 54 | − | − |
| | | 2 | 70 | − | − |
| | | 3 | 74 | − | − |
| | | 4 | 76 | − | − |
| | | 5 | 100 | − | − |
| | | average | 75 | | |

*The case when restoration of electroencephalogram is recognized is judged as +, and the case when not recognized as −.

EXAMPLE 3

Preparation of the prophylactic and therapeutic agent for circulatory disorders of the present invention (1) Tablets The following components were mixed in a conventional manner and tabletted by means of a conventional device.

| | Active ingredient of the invention | 10 mg |
|---|---|---|
| | Crystalline cellulose | 21 mg |
| | Corn starch | 33 mg |
| | Lactose | 65 mg |
| | Magnesium stearate | 1.3 mg |
| (2) | Soft capsules | |

EXAMPLE 2

Protective action for myocardial ischemia

When coronary blood flow transporting nutritions to cardiac muscles is interrupted (disorder in blood flow) or recirculated (disorder in recirculation) by a certain cause, cardiac muscles will be damaged (disorder of mycardial ischemia). The degree of such disorder in cardiac muscles will be advanced as the period of ischemia state is prolonged to cause various ischemic cardiac disorders such as the so-called myocardial infarction and cardiac insufficiency.

Accordingly, the protective effect of the Compound No. 1, as a typical compound, on cardiac muscles were examined as described below.

In the experiment, Wistar strain male rats weighing 300 to 400 g were used. The heart was extirpated into a Krebs-Henseleit bicarbonate (KH) solution which had been oxygenated with 95% $O_2$–5% $CO_2$, under anesthesia by intraperitoneal administration of 50 mg/kg of pentobarbital sodium. Immediately after the isolation, a cannula was intubated into the aorta ascendens, and perfusion was started according to the Langendorff method (75 cm $H_2O$). Subsequently, the cannula was intubated into the left artium. Then, perfusion in accordance with the Langerdorff method was further conducted for 10 minutes, and then the left artium cannula was opened change the mode of perfusion to that of the working heart method (preload 10 cm $H_2O$, afterload 80 cm $H_2O$) (American Journal of Physiology, 212, 804, 1967), which was conducted for 15 minutes. Next, in accordance with the method of Ichihara et al (Journal of Cardiovascular Pharmacology, 5, 745, 1983), the afterload on the aorta was released to provide an ischemic state in the cardiac muscles for 20 minutes. Since five minutes before the initiation of the ischemic state, the perfusate was changed to the one containing the test medicine and such perfusate was used also during the period of the ischemic state. Reperfusion was conducted for 30 minutes with a perfusate containing no test medicine with the afterload of 80 cm $H_2O$. In order to determine the cardiac functions, coronal perfusion flow (CF), cardiac output (CO), heart rate (HR), aorta pressure (AP) and rate pressure product (HR×AP) were measured. The CF was measured by use of a 10 ml measuring cylinder. The CO was measured through a direct blood flow measuring probe (Model FF-030, 30, produced by Nihon Kohden K.K.) disposed immediately in front of the left artium cannula, by use of an electromagnetic blood flow meter (Model MFV-2100, produced by Nihon Kohden K.K.) and an amplifier for bioelectricity (Model AB-621G, produced by Nihon Kohden K.K.). The AP was measured through a pressure transducer (Model MPU-0.5, produced by Nihon Kohden K.K.) connected to the aortic cannula, by use of an amplifier for distortion pressure (Model AP-601G, produced by Nihon Kohden K.K.). The HR was measured by use of an cardiotacho meter (Model AT-601G, produced by Nihon Kohden K.K.). The rate pressure product (HR×AP) was calculated by multiplying the HR by the aortic pressure.

As the perfusate, a KH solution, which had been oxygenated with 95% $O_2$–5% $CO_2$ and heated to 37° C. was used. The formulation of the KH solution (unit: mM) is as follows. NaCl 118, KCl 4.7, $CaCl_2$ 2.5, $MgSO_4$ 1.2, $KH_2PO_4$ 1.2, $NaHCO_3$ 25 and glucose 11.

Compound No. 1, the test medicine, was dissolved in one equivalent of an aqueous 1N-NaOH solution, followed by dilution in the KH solution for use.

Changes in the cardiac functions after treatment with the test medicine and recovery thereof at reperfusion are indicated in terms of percentage based on the value measured before the treatment with the test medicine. The results of the experiments are all shown in terms of the mean ± standard error.

When Compound No. 1 was used in order to find out the degree of the recovery of cardiac functions 30 minutes after reperfusion of the KH solution after the cardiac ischemia loading was effected for 20 minutes, said Compound (1) showed an average recovery action of 24% based on the cardiac output (CO) as an index. However, in the negative control group to which the same flow rate of physiological saline solution was administered in place of the Compound No. 1, said degree was found to be 3% on an average, which is a negligible action (see Table 3).

Table 3: The cardiac output (CO) 30 minutes after the reperfusion after myocardial ischemia loading was effected

|  | N | Recovery of the cardiac output (CO) (%) |
|---|---|---|
| Physiological saline solution | 9 | 2.7 ± 1.8 |
| Compound No. 1 $10^{-5}$ M | 5 | 23.8 ± 14.6 |

In Table 4, there is shown an example wherein the cardiac output (CO) reached 50% or more, 30 minutes after the reperfusion after ischemic loading was effected as an example of the recovery of the cardiac functions.

TABLE 4

|  | Number of recovery of the cardiac functions (%) |
|---|---|
| Physiological saline solution | 0/9 (0) |
| Compound No. 1 | 2/5 (40) |

The above results demonstrate that Compound (1) exhibits protective action for myocardial ischemia.

The following components were mixed in a conventional manner and filled in soft capsules.

| Active ingredient of the invention | 10 mg |
|---|---|
| Olive oil | 105 mg |
| Lecithin | 6.5 mg |

(3) Preparation for injection

The following components were mixed in a conventional manner and 1 mg ampoules were prepared.

| Active ingredient of the invention | 0.7 mg |
|---|---|
| Sodium chloride | 3.5 mg |
| Distilled water for injection | 1.0 ml |

We claim:

1. A prophylactic and therapeutic pharmaceutical composition for inhibiting lipid peroxidation by active oxygen, which results from ischemia, comprising: an effective amount of a pyrazoline derivative to inhibit lipid peroxidation by active oxygen, of the formula:

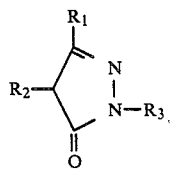

wherein $R_1$ represents a hydrogen atom, an aryl group, an alkyl group having 1 to 5 carbon atoms; $R_2$ represents a hydrogen atom, an aryloxy group, an alkyl group having 1 to 5 carbon atoms; or $R_1$ and $R_2$ taken together represent an alkylene group having 3 to 5 carbon atoms; $R_3$ represents a cycloalkyl group having 5 to 7 carbon atoms, a naphthyl group, or a phenyl group which is unsubstituted or para or meta substituted with 1 to 3 substituents which are the same or different selected from the group consisting of alkyl groups having 1 to 5 carbon atoms, alkoxy groups having 1 to 5 carbon atoms, alkoxycarbonyl groups having a total carbon number of 2 to 5, alkylmercapto groups having 1 to 3 carbon atoms, halogen atoms, a trifluoromethyl group, a carboxyl group, a cyano group, a hydroxyl group, a nitro group or a pharmaceutically acceptable salt thereof as an active ingredient in a pharmaceutical carrier.

2. A method for inhibiting the formation of peroxidized lipids in a mammal, as a result of ischemia, comprising administering an effective amount of a pyrazolone derivative of the formula:

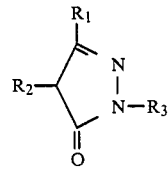

wherein $R_1$ represents a hydrogen atom, an aryl group, an alkyl group having 1 to 5 carbon atoms; $R_2$ represents a hydrogen atom, an aryloxy group, an alkyl group having 1 to 5 carbon atoms; or $R_1$ and $R_2$ taken together represent an alkylene group having 3 to 5 carbon atoms; $R_3$ represents a cycloalkyl group having 5 to 7 carbon atoms, a naphthyl group, or a phenyl group which is unsubstituted or para or meta substituted with 1 to 3 substituents which are the same or different selected from the group consisting of alkyl groups having 1 to 5 carbon atoms, alkoxy groups having 1 to 5 carbon atoms, alkoxycarbonyl groups having a total carbon number of 2 to 5, alkylmercapto groups having 1 to 3 carbon atoms, halogen atoms, a trifluoromethyl group, a carboxyl group, a cyano group, a hydroxyl group, a nitro group or a pharmaceutically acceptable salt thereof as an active ingredient in a pharmaceutical carrier.

3. A prophylactic and therapeutic pharmaceutical composition for inhibiting the formation of peroxidized lipids in a mammal and simultaneously providing antagonistic action against drowsy pattern in an electroencephalogram caused by barbituates, comprising an effective amount of a pyrazolone derivative of the formula:

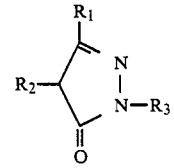

wherein $R_1$ represents a hydrogen atom, an aryl group, an alkyl group having 1 to 5 carbon atoms; $R_2$ represents a hydrogen atom, an aryloxy group, an alkyl group having 1 to 5 carbon atoms; or $R_1$ and $R_2$ taken together represent an alkylene group having 3 to 5 carbon atoms; $R_3$ represents a cycloalkyl group having 5 to 7 carbon atoms, a naphthyl group, or a phenyl group which is unsubstituted or para or meta substituted with 1 to 3 substituents which are the same or different selected from the group consisting of alkyl groups having 1 to 5 carbon atoms, alkoxy groups having 1 to 5 carbon atoms, alkoxycarbonyl groups having a total carbon number of 2 to 5, alkylmercapto groups having 1 to 3 carbon atoms, halogen atoms, a trifluoromethyl group, a carboxyl group, a cyano group, a hydroxyl group, a nitro group or a pharmaceutically acceptable salt thereof as an active ingredient in a pharmaceutical carrier.

4. A method for inhibiting the formation of peroxidized lipids in a mammal and simultaneously to provide antagonistic action against drowsy pattern in an electroencephalogram caused by barbituates, comprising administering an effective amount of a pyrazolone derivative of the formula:

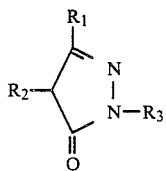

wherein $R_1$ represents a hydrogen atom, an aryl group, an alkyl group having 1 to 5 carbon atoms; $R_2$ represents a hydrogen atom, an aryloxy group, an alkyl group having 1 to 5 carbon atoms; or $R_1$ and $R_5$ taken together represent an alkylene group having 3 to 5 carbon atoms; $R_3$ represents a cycloalkyl group having 5 to 7 carbon atoms, a naphthyl group, or a phenyl group which is unsubstituted or para or meta substituted with 1 to 3 substituents which are the same or different selected from the group consisting of alkyl groups having 1 to 5 carbon atoms, alkoxy groups having 1 to 5 carbon atoms, alkoxycarbonyl groups having a total carbon number of 2 to 5, alkylmercapto groups having 1 to 3 carbon atoms, halogen atoms, a trifluoromethyl group, a carboxyl group, a cyano group, a hydroxyl group, a nitro group or a pharmaceutically acceptable salt thereof as an active ingredient in a pharmaceutical carrier.

5. The composition according to claim 1 or 3, wherein the aryl group represented by $R_1$ is a phenyl group or phenyl groups which are substituted with a methyl group, a butyl group, a methoxy group, a butoxy group, a hydroxyl group or a chlorine atom; the alkyl group having 1 to 5 carbon atoms represented by $R_1$, $R_2$ or $R_3$ is a methyl group, an ethyl group, a propyl group, an isopropyl group, a butyl group, an isobutyl group, a sec-butyl group, a tert-butyl group or a pentyl group; the alkoxycarbonylalkly group having total carbon number of 3 to 6 represented by $R_1$ is a methoxycabonylmethyl group, an ethoxycarbonylmethyl group, a propoxycarbonylmethyl group, a methoxycarbonylethyl group or a methoxycarbonylpropyl group; the aryloxy group represented by $R_2$ is a phenoxy group, a p-methylphenoxy group, a p-methoxyphenoxy gorup, a p-chlorophenoxy group or a p-hydroxyphenoxy group; the arylmercapto group represented by $R_2$ is a phenylmercapto group, a p-methylphenylmercapto group, a p-methoxyphenylmercapto group, a p-chlorophenylmercapto group or a p-hydroxphenylmercapto group; the hydroxyalkyl group having 1 to 3 carbon atoms represented by $R_2$ $R_3$ is a hydroxymethyl group, a 2-hydroxyethyl group or a 3-hydroxpropyl group; the cycloalkyl group having 5 to 7 carbon atoms represented by $R_3$ is a cyclopentyl group, a cyclohexyl group or a cycloheptyl group; as the substituent for the phenyl group in the definition of $R_3$, the alkoxy group having 1 to 5 carbon atoms is a methoxy group, an ethoxy group, a propoxy group, an isopropoxy group, a butoxy group or a pentyloxy group; the alkoxycarbonyl group having a total carbon number of 2 to 5 is a methoxycarbonyl group, an ethyoxycarbonyl group, a propoxycarbonyl group or a butoxycarbonyl group; the alkylmercapto group having 1 to 3 carbon atoms is a methylmercapto group, an ethylmercapto group or a propylmercapto group; the alkylamino group having 1 to 4 carbon atoms is a methylamino group, an ethylamino group, a propylamino group or a butylamino group; and the dialkylamino group having a total carbon number of 2 to 8 is a diemthylamino group, a diethylamino group, a dipropylamino group or a dibutylamino group.

6. The composition according to claim 1 or 3, wherein said pyrazolone derivative is selected from the group consisting of:
   3-Methyl-1-phenyl-2-pyrazolin-5-one;
   3-Methyl-1-(4-methylphenyl)-2-pyrazolin-5-one;
   1-(4-Methoxyphenyl)-3-methyl-2-pyrazolin-5-one;
   1-(4-Ethoxyphenyl)-3-methyl-2-pyrazolin-5-one;
   1-(4-Chlorophenyl)-3-methyl-2-pyrazolin-5-one;
   1-Phenyl-3-propyl-3-pyrazolin-5-one;
   3,4-Dimethyl-1-phenyl-2-pyazolin-5-one;
   4-Isobutyl-3-methyl-1-phenyl-2-pyrazolin-5-one;
   3,3a,4,5,6,7-Hexahydro-2-phenyl-2H-indazol-3-one; and
   1-Cyclohexyl-3-methyl-2-pyazolin-5-one
or a pharmaceutically acceptable salt thereof.

7. The composition according to claim 1 or 3, wherein said circulatory disorders are ischematic diseases.

8. The composition according to claim 1 or 3, wherein said agent is useful as an inhibitor against lipid peroxidation.

9. The composition according to claim 1 or 3, wherein 3-methyl-1-phenyl-2-pyrazolin-5-one or a pharmaceutically acceptable salt thereof as an active ingredient is useful as an agent for normalizing cerebral functions.

10. The method of claim 2 or 4, wherein said pyrazolone derivative is 3-methyl-1-phenyl-2-pyrazolin-5-one.

11. The method of claim 2 or 4, wherein said pyrazolone derivative is 3-methyl-1-(4-methylphenyl)-2-pyrazolin-5-one.

12. The method of claim 2 or 4, wherein said pyrazolone derivative is 1-(4-methoxyphenyl)-3-methyl-2-pyrazolin-5-one.

13. The method of claim 2 or 4, wherein said pyrazolone derivative is (4-ethoxyphenyl)-3-methyl-2-pyrazolin-5-one.

14. The method of claim 2 or 4, wherein said pyrazolone derivative is 1-(4-chlorophenyl)-3-methyl-2-pyrazolin-5-one.

15. The method of claim 2 or 4, wherein said pyrazolone derivative is 1-phenyl-3-propyl-2-pyazolin-5-one.

16. The method of claim 2 or 4, wherein said pyrazolone derivative is 3,4-dimethyl-1-phenyl-2-pyazolone-5-one.

17. The method of claim 2 or 4, wherein said pyrazolone derivative is 4-isobutyl-3-methyl-1-phenyl-2-pyrazolin-5-one.

18. The method of claim 2 or 4, wherein said pyrazolone derivative is 3,3a,4,5,6,7-hexahydro-2-phenyl-2H-indazol-3-one.

19. The method of claim 2 or 4, wherein said pyrazolone derivative is 1-cyclohexyl-3-methyl-2-pyrazolin-5-one.

* * * * *

UNITED STATES PATENT AND TRADEMARK OFFICE
CERTIFICATE OF CORRECTION

PATENT NO. : 4,857,542

DATED : August 15, 1989

INVENTOR(S) : NISHI et al

Page 1 of 2

It is certified that error appears in the above-identified patent and that said Letters Patent is hereby corrected as shown below:

Column 23, lines 30-44, delete all of the subject matter on these lines.

Column 24, line 68, replace "Table 3" with --Table 5--.

Column 25, line 1, replace "Table 3" with --Table 5--.

Column 25, line 13, replace "Table 4" with --Table 6--.

Column 25, line 18, replace "TABLE 4" with --TABLE 6--.

UNITED STATES PATENT AND TRADEMARK OFFICE
CERTIFICATE OF CORRECTION

PATENT NO. : 4,857,542

DATED : August 15, 1989

INVENTOR(S) : Nishi, et al

It is certified that error appears in the above-identified patent and that said Letters Patent is hereby corrected as shown below:

Column 25, between lines 26 and 27 insert the following

-- EXAMPLE 3

Preparation of the prophylactic and therapeutic agent for circulatory disorders of the present invention (1) Tablets The following components were mixed in a conventional manner and tabletted by means of a conventional device.

| | |
|---|---|
| Active ingredient of the invention | 10 mg |
| Crystalline cellulose | 21 mg |
| Corn starch | 13 mg |
| Lactose | 65 mg |
| Magnesium stearate | 1.3 mg |

(2) Soft capsules --

Signed and Sealed this

Fifth Day of January, 1993

*Attest:*

DOUGLAS B. COMER

*Attesting Officer*     Acting Commissioner of Patents and Trademarks